United States Patent [19]
Smith et al.

[11] Patent Number: 5,508,269
[45] Date of Patent: Apr. 16, 1996

[54] AMINOGLYCOSIDE FORMULATION FOR AEROSOLIZATION

[75] Inventors: Arnold L. Smith, Columbia, Mo.; Bonnie W. Ramsey, Seattle; Alan B. Montgomery, Bellevue, both of Wash.

[73] Assignee: Pathogenesis Corporation, Seattle, Wash.

[21] Appl. No.: 325,705

[22] Filed: Oct. 19, 1994

[51] Int. Cl.$^6$ .............................. A61K 9/12; A61K 31/73
[52] U.S. Cl. .............................................. 514/38; 514/956
[58] Field of Search ........................................ 514/38, 956

[56] References Cited

U.S. PATENT DOCUMENTS

| | | | |
|---|---|---|---|
| 4,424,216 | 1/1984 | Cerami et al. | 424/211 |
| 5,006,343 | 4/1991 | Benson et al. | 424/450 |

OTHER PUBLICATIONS

Margaret E. Hodson, et al., *Aerosol Carbenicillin and Gentamicin Treatment of Pseudomonas aeruginosa Infection in Patients with Cystic Fibrosis*, The Lancet, pp. 1137–1139, Nov. 21, 1981.

David Stephens, et al., *Efficacy of inhaled tobramycin in the treatment of pulmonary exacerbations in children with cystic fibrosis*, Pediatric Infectious Diseases, vol. 2, No. 3, pp. 209–211, May 1983.

Jack Levy, et al., *Bioactivity of Gentamicin in Purulent Sputum from Patients with Cystic Fibrosis or Bronchiectasis: Comparison with Activity in Serum*, The Journal of Infectious Diseases, vol. 148, No. 6, pp. 1069–1075, Dec. 1993.

Michael A. Wall, *Inhaled Antibiotics in Cystic Fibrosis*, The Lancet, Jun. 11, 1993.

Paul M. Mendelman, et al., *Aminoglycoside Penetration, Inactivation, and Efficacy in Cystic Fibrosis Sputum$^{1-3}$*, Am. Rev. Respir. Diseases, 132:761–765, 1985.

P. Kun, et al., *Nebulized gentamicin in children and adolescents with cystic fibrosis*, Aust. Paediatr. J., 20:43–45, 1984.

Ian MacLusky, et al., *Inhaled antibiotics in cystic fibrosis: Is there a therapeutic effect?*, J. Pediatr., 108(2):861–865, 1986.

F. Carswell, et al. *A Controlled Trial of Nebulized Aminoglycoside and Oral Flucloxacillin Versus Placebo in the Outpatient Management of Children with Cystic Fibrosis*, Br. J. Dis. Chest, 81, 356–360, 1987.

S. P. Newman, et al., *Deposition of carbenicillin aerosols in cystic fibrosis: effects of nebuliser system and breathing pattern*, Thorax, 43:318–322, 1988.

Gratiana Steinkamp, et al., *Long–term Tobramycin Aerosol Therapy in Cystic Fibrosis*, Pediatric Pulmonary, 6:91–98, 1989.

Arnold L. Smith, et al., *Safety of Aerosol Tobramycin for 3 Months to Patients with Cystic Fibrosis*, Pediatric Pulmonary, 7:265–271, 1989.

Ian B. MacLusky, et al., *Long–Term Effects of Inhaled Tobramycin in Patients with Cystic Fibrosis Colonized with Pseudomonas aeruginosa*, Pediatric Pulmonology, 7:42–48, 1989.

*Pulmonary Disorders Cystic Fibrosis (CF)*, The Merck Manual, 16th Edition, Chapter 196, pp. 2207–2211, 1992.

Bonnie W. Ramsey, *Efficacy of Aerosolized Tobramycin in Patients with Cystic Fibrosis*, New England Journal of Medicine, 328:1740–1746, Jun. 17, 1993.

Physicians' Desk Reference, 48th Edition, pp. 472–473, 914–917, 1250–1253, (1994).

Stephen G. Jenkins, *Aerosolized Amikacin Administration to Cystic Fibrosis Patients Chronically Infected with Pseudomonas aeruginosa*, p. 147, Presented at the 26th Annual Meeting of the Cystic Fibrosis Foundation, Anaheim, California, May 16–19, 1985. Abstract.

Ian Nathanson, et al., *Effectiveness of Aerosolized Gentamicin in Cystic Fibrosis (CF)*, p. 145, Presented at the 26th Annual Meeting of the Cystic Fibrosis Foundation, Anaheim, California, May 16–19, 1985. Abstract.

Chun–I Wang, et al., *The Effect of Tobramycin Aerosol to Pulmonary Infection from Pseudomonas aeruginosa in Patients with Cystic Fibrosis (CF)*, p. 159, Presented at the 25th Annual Meeting of the Cystic Fibrosis Foundation, San Jose, California, Apr. 27–30, 1984. Abstract.

Martha N. Franz, et al., *Evaluation of Tobramycin Aerosol Therapy in Cystic Fibrosis (CF)*, p. 143, Presented at the 26th Annual Meeting of the Cystic Fibrosis Foundation, Anaheim, California, May 16–19, 1985. Abstract.

*Primary Examiner*—Richard L. Raymond
*Attorney, Agent, or Firm*—Hana Verny

[57] ABSTRACT

An aminoglycoside formulation for delivery by aerosolization. The concentrated aminoglycoside formulation containing an efficacious amount of aminoglycoside able to inhibit 95–100% of susceptible bacteria. Aminoglycoside formulated in 5 ml solution of a quarter normal saline having pH between 5.5 and 6.5. The method for treatment of endobronchial infections by a produced by a formulation delivered as an aerosol having mass medium average diameter predominantly between 1 to 5 μ, produced by a jet or ultrasonic nebulizer.

16 Claims, 3 Drawing Sheets

AMINOGLYCOSIDE FORMULATION FOR AEROSOLIZATION

This invention was made with government support under Grant No. HL 50253, awarded by the National Institute of Health. The United States Government may have certain rights in this invention.

BACKGROUND OF THE INVENTION

1. Field of Invention

The current invention concerns novel and improved aminoglycoside formulation for delivery by aerosolization. In particular, the invention concerns the formulation consisting of a concentrated solution of the aminoglycoside formulated in 5 ml of a quarter normal saline having pH between 5.5 and 6.5. The formulation permits and is suitable for delivery of the aminoglycoside to the lung endobronchial space of airways in an aerosol having mass medium average diameter predominantly between 1 to 5 $\mu$. The formulated and delivered efficacious amount of the aminoglycoside is sufficient for treatment and prophylaxis of acute and chronic endobronchial infections, particularly those caused by the bacterium *Pseudomonas aeruginosa*. The novel formulation has small volume yet delivers effective dose of aminoglycoside to the site of the infection.

BACKGROUND ART AND RELATED ART DISCLOSURES

*Pseudomonas aeruginosa* grows in the endobronchial space and is found in the sputum of infected individuals. During exacerbations of infection, such growth also occurs in the alveoli. The most common representative disease of bacterial *Pseudomonas aeruginosa* endobronchial infection is cystic fibrosis.

Cystic fibrosis (CF) is a common genetic disease that is characterized by the inflammation and progressive destruction of lung tissue. The debilitation of the lungs in CF patients is associated with accumulation of purulent sputum produced as a result of chronic endobronchial infections caused by H. influenzae, staphylococcus aureaus and *Pseudomonas aeruginosa*. Nearly all individuals suffering from CF eventually die of respiratory failure. The advent of antipseudomonal antibiotic aminoglycosides such as tobramycin has decreased the mortality of CF patients and increased their life-span.

Tobramycin is an aminoglycoside specifically active against *Pseudomonas aeruginosa*. When delivered parenterally for a short period of time, it has been shown to successfully treat exacerbations which occur in patients with CF.

Presently, parenteral administration of an aminoglycoside and a beta-lactam active against *Pseudomonas aeruginosa* is the treatment of choice for chronic bronchitis or bronchiectasis seen in CF patients. However, aminoglycoside penetration into the bronchial secretions is poor at approximately only about 12% of the peak serum concentration (*Rev. Infect. Dis.*, 3:67 (1981)). According to *Advances in Pediatric Infections Diseases*, 8:53 (1993), sputum itself is inhibitory to the bioactivity of aminoglycosides because of its high ionic strength and the presence of divalent cations. Sputum also contains mucin glycoproteins and DNA, which bind aminoglycosides. This inhibitory activity can be overcome by increasing the concentration of aminoglycosides in the sputum to ten times the minimum inhibitory concentration of the particular *Pseudomonas aeruginosa* isolate (*J. Infect. Dis.*, 148:1069 (1983)).

Aminoglycosides penetrate poorly into the sputum and therefore, to achieve therapeutic concentrations in sputum, high doses parenteral administration are required. This increases the risk of systemic toxicity including ototoxicity and nephrotoxicity because the serum contains high aminoglycoside concentrations. Intravenous therapy may increase hardship on the patient, frequently requires hospitalization, which increases treatment costs and exposes the patient to potential other infections.

Attempts were made previously to administer aminoglycoside by aerosol. When high doses of aminoglycosides, such as tobramycin, are administered to the lungs by aerosolization, sputum levels of tobramycin are maximized and serum levels are minimized. Thus, administration of aminoglycoside by aerosolization has the advantage of reducing systemic toxicity while providing efficacious concentrations of the antibiotic in sputum. The bronchial barrier restricts the movement of aerosolized aminoglycoside and prevents aminoglycoside from reaching high systemic levels. Unfortunately, the physical properties of aminoglycosides require relatively high dose of the drug for aerosolization and such treatment then becomes rather expensive.

One of the first studies using aerosolized antibiotics for the treatment of CF was reported in *Lancet*, 22:1377–9 (1981). A controlled, double-blind study on twenty CF patients demonstrated that aerosol administration of carbenicillin and the aminoglycoside gentamicin can improve the health of CF patients. Since that time, scattered reports in the literature have examined aerosol delivery of aminoglycosides in general and tobramycin in particular. However, a clinical evaluation and comparison of these studies is often difficult because of the differences in antibiotic formulations, breathing techniques, nebulizers and compressors. Moreover, the aerosol delivery is often difficult to evaluate because of the formulations, aerosolized devices, dosages, particle sizes regimens, etc. differ. When, for example, the aerosol contains a large number of particles with a MMAD greater than 5 $\mu$, these are deposited in the upper airway decreasing the amount of antibiotic delivered to the site of infection in the lower respiratory tract. Article published in *Arch. Dis. Child.*, 68:788 (1993) emphasized the need for standardized procedures and for improvement in aerosol administration of drugs to CF patients.

Aerosolization of tobramycin has specifically been attempted and used with CF patients to suppress *Pseudomonas aeruginosa* infections and thereby decrease lung inflammation and improve lung function.

Aerosolization of aminoglycosides has the advantage of being able to deliver high concentrations of the drug directly to the airways with low systemic absorption. This would allow for the development of a safer, long-term therapy. Effective aerosol administration is, however, currently compromised by the lack of additive-free and physiologically balanced formulations and particularly by inability of certain nebulizers to generate small and uniform particle size aerosols. A range of aerosolized particles needed to deliver the drug to the endobronchial space, the site of the infection is 1–5 $\mu$. Many nebulizers which aerosolize aminoglycosides produce large number of aerosol particles in the range of 50–100 $\mu$. In order to be therapeutically effective, the majority of aerosolized aminoglycoside particles should not have larger MMAD than between 1 and 5 $\mu$. When the aerosol contains a large number of particles with a MMAD larger than 5 $\mu$, these are deposited in the upper airways decreasing the amount of antibiotic delivered to the site of infection in the lower respiratory tract. Although aminoglycosides are not very readily absorbed systemically across the mucous membrane, there is still a certain risk of systemic toxicity developing in some patients.

The plugging the smaller bronchi or bronchioli and thus preventing a delivery of the drug into an endobronchial space where the bacterium resides is one potential limitation associated with aerosols which are currently available and utilized for treatment of *Pseudomonas aeruginosa* infections. Additionally, a waste of the drug occurring during delivery of the larger particles to places where the drug is not effective generates substantial economical loss and increases the cost of the treatment.

Currently, two types of available nebulizers, jet and ultrasonic, can produce and deliver aerosol particles having sizes between 1 and 5 μ. These are particle size optimal for treatment of *Pseudomonas aeruginosa* infections. However, these nebulizers are unable to deliver the aminoglycosides and particularly tobramycin in any efficient manner as they are unable to nebulize small volumes of concentrated aminoglycoside formulated in standard way in normal saline solution.

Typically, prior art aerosolization of the aminoglycosides, such as tobramycin, could only utilize formulations containing high volumes, such as for example the formulation suitable for aerosolization by DeVilbiss ultrasonic nebulizer where 20 mg of tobramycin was formulated per 1 ml of normal saline, in large, 30 ml volumes. This leads to accumulation of unnecessarily high concentration of drug in sputum, to development of side effects, to a waste of drug, extension of treatment time, demands for large volume handling nebulizers and in general it is costly, laborious and impractical. The requirement for large volume handling nebulizers complicates or eliminates their use in home or ambulatory setting, thus necessitating doctor office visit or hospital.

Therefore, it would be highly advantageous to provide the formulation which could be efficiently aerosolized in both a jet and ultrasonic nebulizer.

Another requirement for an acceptable formulation is its adequate shelf life. Generally, aminoglycoside and particularly tobramycin intravenous solutions contain phenol or other preservatives to maintain potency and to minimize the production of degradation products that may color the aminoglycoside solution. However, phenol and other preservatives, when aerosolized, may induce bronchospasm, an unwanted occurrence in patients with lung diseases such as cystic fibrosis.

It would be highly advantageous, therefore to provide an aminoglycoside formulation containing no preservatives, whose pH is adjusted to levels which slows or prevents discoloration, thereby providing adequate shelf life of the formulation suitable for commercial distribution, storage and use.

In consideration of all problems and disadvantages connected with prior art aminoglycoside aerosol delivery, it would be highly advantageous to provide a formulation and the system for delivery of sufficient dose of aminoglycosides such as tobramycin in concentrated form, containing the smallest possible volume of the solution which can be aerosolized and delivered predominantly to the endobronchial space.

It is therefore a primary object of this invention to provide a concentrated formulation of the aminoglycoside, which contains sufficient but not excessive concentration of the drug which can be efficiently aerosolized by nebulization in both jet and ultrasonic nebulizers into aerosol particle sizes predominantly within a range from 1 to 5 μ and which salinity is adjusted to permit generation of an aminoglycoside aerosol well tolerated by patients, which formulation further has an adequate shelf life.

All patents, patent applications and publications cited herein are hereby incorporated by reference in their entirety.

SUMMARY

One aspect of the current invention is a concentrated formulation suitable for efficacious delivery of aminoglycoside into endobronchial space of a patient suffering from bacterial endobronchial infection.

Another aspect of the current invention is a formulation suitable for efficacious delivery of tobramycin into endobronchial space of a patient suffering from bacterial *Pseudomonas aeruginosa* endobronchial infection.

Still another aspect of the current invention is a formulation comprising from 40–100 mg of aminoglycoside in 1 ml of saline diluted into a quarter normal saline strength wherein said formulation has a pH between 5.5 and 6.5 and is delivered in 5 ml concentrated form by aerosolization.

Still another aspect of the current invention is a formulation comprising from 50–70 mg of tobramycin in 1 ml of saline diluted into an appropriate strength balancing osmolarity, ionic strength and chloride concentration to tolerable values wherein said formulation has a pH between 5.5 and 6.5 and is delivered in 5 ml concentrated form by aerosolization.

Still another aspect of the current invention is a formulation comprising 60–80 mg of aminoglycoside in 1 ml of saline diluted into a quarter normal saline strength wherein said formulation has a pH between 5.5 and 6.5 and is delivered in 5 ml concentrated form in an aerosol particles having the mass medium average diameter predominantly between 1 and 5 μ, wherein said formulation is nebulized using a jet or ultrasonic nebulizer.

Still another aspect of the current invention is a formulation comprising 60 mg of tobramycin in 1 ml of saline diluted into a quarter normal saline strength wherein said formulation has a pH between 5.5 and 6.5 and is delivered in 5 ml concentrated form in an aerosol particles having the mass medium average diameter predominantly between 1 and 5 μ, wherein said formulation is nebulized using a jet or ultrasonic nebulizer.

Still another aspect of the current invention is a method for treatment of pulmonary infections caused by susceptible bacteria by administering to a subject requiring such treatment a formulation comprising 40–100 mg of aminoglycoside in 1 ml of saline diluted into a quarter normal saline strength wherein said formulation has a pH between 5.5 and 6.5 and is delivered by a jet or ultrasonic nebulizer in 5 ml concentrated form in an aerosol producing a particle size having the mass medium average diameter predominantly between 1 and 5 μ.

Still another aspect of the current invention is a method for treatment of pulmonary infections caused by *Pseudomonas aeruginosa* by administering to a subject requiring such treatment a formulation comprising 60 mg of tobramycin in 1 ml of saline diluted into a quarter normal saline strength wherein said formulation has a pH between 5.5 and 6.5 and is delivered by a jet nebulizer in 5 ml concentrated form in an aerosol producing a particle size having the mass medium average diameter predominantly between 1 and 5 μ.

DEFINITIONS

As used herein:

"Normal saline" means water solution containing 0.9% NaCl.

"Diluted saline" means normal saline containing 0.9% NaCl diluted into its lesser strength.

"Quarter normal saline" or "¼ NS" means normal saline diluted to its quarter strength containing 0.225% NaCl.

DETAILED DESCRIPTION OF THE INVENTION

The current invention concerns a concentrated aminoglycoside formulation suitable for efficacious delivery of the aminoglycoside by aerosolization into endobronchial space. The invention is most preferably suitable for formulation of concentrated tobramycin for aerosolization by jet or ultrasonic nebulizers to produce tobramycin aerosol particle size between 1 and 5 μ necessary for efficacious delivery of tobramycin into endobronchial space to treat *Pseudomonas aeruginosa* infections. The formulation contains minimal yet efficacious amount of aminoglycoside formulated in smallest possible volume of physiologically acceptable solution having a salinity adjusted to permit generation of aminoglycoside aerosol well-tolerated by patients but preventing the development of secondary undesirable side effects such as bronchospasm and cough.

Primary requirements for any aerosolized formulation are its safety and efficacy. Additional advantages are lower cost, practicality of use, long-shelf life, storage and manipulation of nebulizer.

The aerosol formulation is nebulized predominantly into particle sizes which can be delivered to the terminal and respiratory bronchioles where the *Pseudomonas aeruginosa* bacterium or other susceptible bacteria reside in patients with cystic fibrosis.

Figure 1:
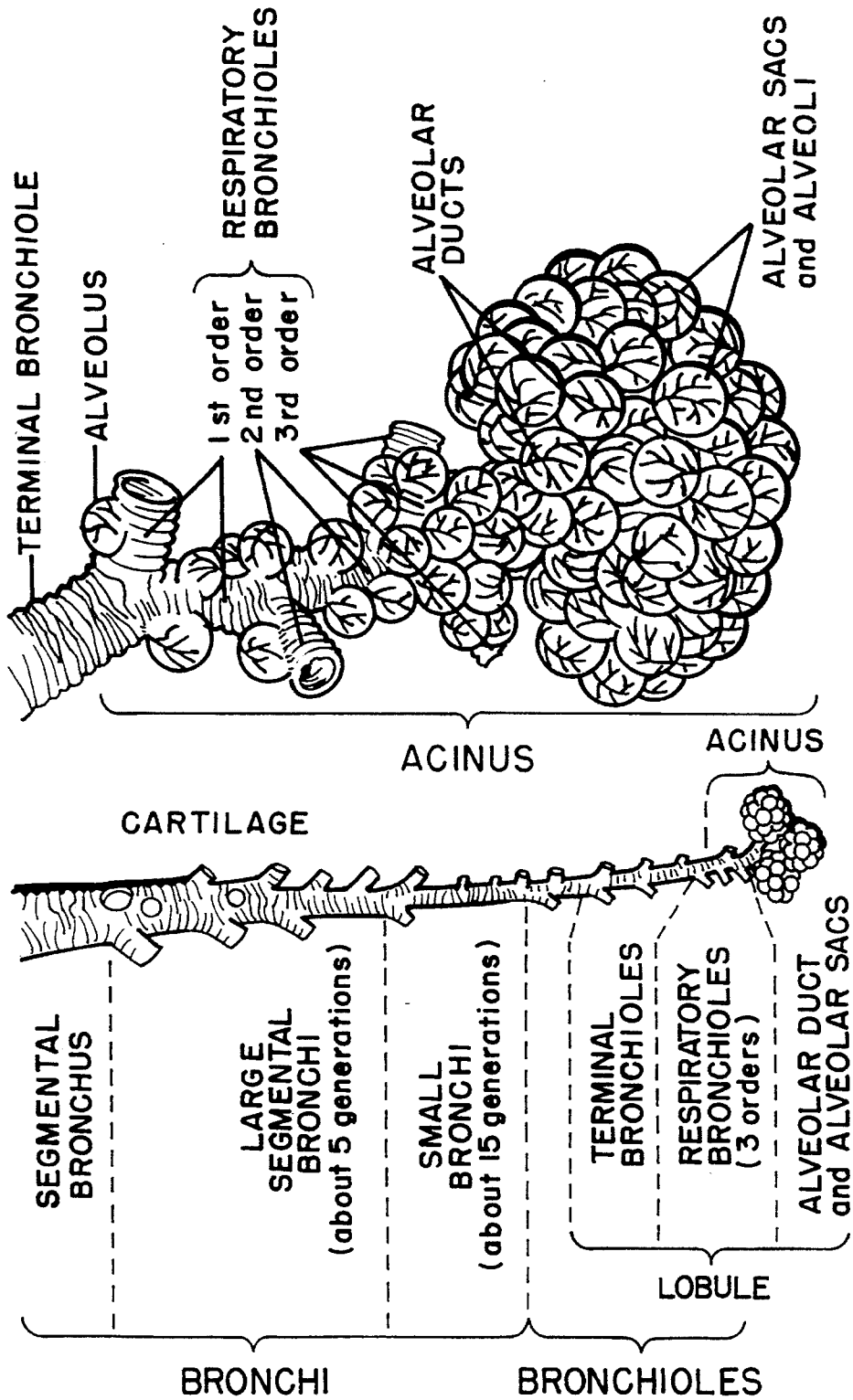
FIG. 1 depicts subdivisions and structure of intrapulmonary airways.

Subdivision and structure of intrapulmonary airways are seen in FIG. 1. *Pseudomonas aeruginosa* is present throughout in airways down to bronchi and bronchioli. However, it is most predominant in terminal and respiratory bronchioles. During exacerbation of infection, bacteria can also be present in alveoli. It is therefore clear that any therapeutic formulation must be delivered throughout the endothelial tree to the terminal bronchioles.

Aerosolized aminoglycoside formulation is formulated for efficacious delivery of aminoglycoside to the lung endobronchial space. A specific jet or ultrasonic nebulizer is selected allowing the formation of the aminoglycoside aerosol particles having mass medium average diameter predominantly between 1 to 5 μ. The formulated and delivered amount of aminoglycoside is efficacious for treatment and prophylaxis of endobronchial infections, particularly those caused by the bacterium *Pseudomonas aeruginosa* when the aminoglycoside tobramycin is used. The formulation has salinity adjusted to permit generation of aminoglycoside aerosol well-tolerated by patients. Further, the formulation has balanced osmolarity ionic strength and chloride concentration. The formulation has a smallest possible aerosolizable volume able to deliver effective dose of aminoglycoside to the site of the infection. Additionally, the aerosolized formulation does not impair negatively the functionality of the airways and does not cause an undesirable side effects.

I. Aerosol Aminoglycoside Formulation

Aminoglycosides of the invention are antibiotics, such as gentamycin, amikacin, kanamycin, streptomycin, neomycin, netilmicin and tobramycin.

The formulation according to the invention contains from 200–500, preferably 300 mg of aminoglycoside sulfate per 5 ml of the quarter normal saline. This corresponds to 40–100, preferably 60 mg/ml of aminoglycoside, which is minimal yet efficacious amount of aminoglycoside to suppress the *Pseudomonas aeruginosa* infections in endobronchial space.

Typically, about three hundred mg of aminoglycoside is dissolved in 5 ml solution of a diluted, typically quarter normal saline containing about 0.225% NaCl. It has been now discovered that a quarter normal saline, that is 0.225% of sodium chloride, is a most suitable vehicle for delivery of aminoglycoside into endobronchial space.

The effective dose for each individual aminoglycoside will depend on its effectivity and intended use. For example, gentamycin is optimally used in 80 mg/ml dosage, while tobramycin is optimally used in 60 mg/ml dosage at least for treatment of endobronchial infection.

II. Aerosol Tobramycin Formulation

Figure 2:
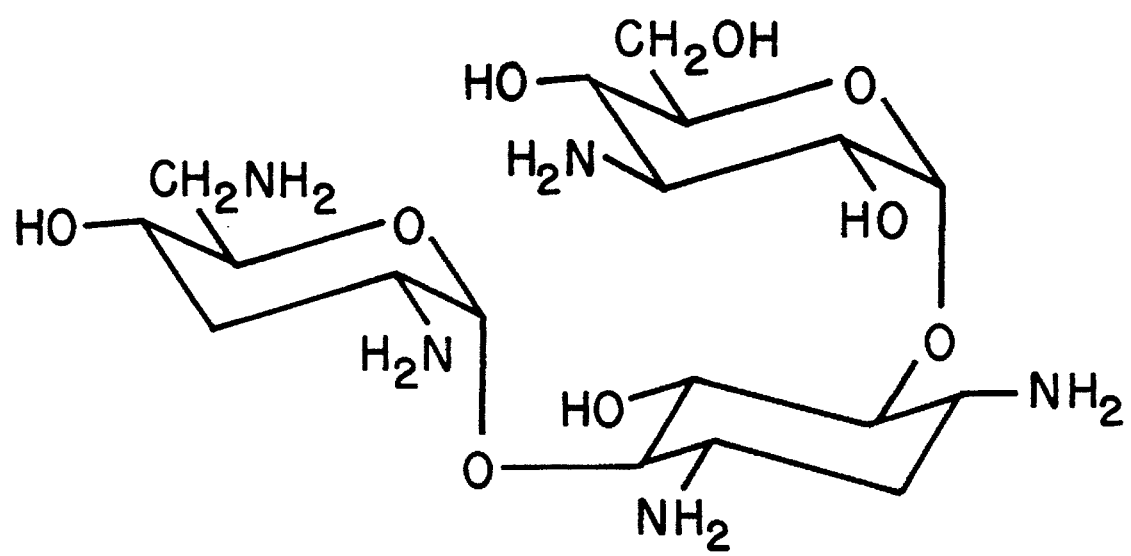
FIG. 2 illustrates a structure of tobramycin.

Tobramycin is an aminoglycoside having a chemical structure shown in FIG. 2. Tobramycin is a drug choice for treatment and prevention of endobronchial *Pseudomonas aeruginosa* infections.

Typically, two to four, preferably 300 mg of tobramycin is dissolved in 5 ml solution of a diluted quarter normal saline, preferably containing 0.225% NaCl.

The most preferred aerosol tobramycin formulation according to the invention contains 300 mg of tobramycin sulfate per 5 ml of the quarter normal saline. This corresponds to 60 mg/ml of tobramycin which is minimal yet efficacious amount of tobramycin to suppress the *Pseudomonas aeruginosa* infections in endobronchial space.

Jet and ultrasonic nebulizers are sensitive to the osmolarity of the formulation. Ultrasonic nebulizers are additionally sensitive to the pH of the formulation and to its ionic strength and therefore it is sometimes difficult to aerosolize aminoglycoside such as tobramycin formulated in normal saline. It has now been discovered that this problem is conveniently solved by formulating aminoglycosides is quarter normal saline, that is saline containing 0.225% of sodium chloride, and that ¼ N saline is a suitable vehicle for delivery of tobramycin into endobronchial space.

Cystic fibrosis patients and other patients with chronic endobronchial infections have high incidence of bronchospastic or asthmatic airways. These airways are sensitive to hypotonic or hypertonic aerosols, to the presence of a permanent ion, particularly a halide such as chloride, as wells as to aerosols that are acidic or basic. The effects of irritating the airways can be clinically manifested by cough or bronchospasm. Both these conditions prevent efficient delivery of aerosolized tobramycin into the endobronchial space.

The tobramycin formulation containing ¼ NS with 60 mg of tobramycin per ml of ¼ NS has an osmolarity in the range of 165–190 Mosm/l. This is within the safe range of aerosols administered to a cystic fibrosis patient. The safety of this solution has been studied and proven. The study is described in Example 4. A further advantage of 0.225% NS solution with 60 mg/ml tobramycin is that this formulation is more efficiently nebulized by an ultrasonic nebulizer compared to tobramycin formulated in a solution 0.9% normal saline as shown in Example 2. Consequently, lesser amount up to one-half of drug is needed.

The pH of the formulation is equally important for aerosol delivery. As noted above, when the aerosol is either acidic or basic, it can cause bronchospasm and cough. The safe range of pH is relative; some patients will tolerate a mildly acidic aerosol which in others will cause bronchospasm. Any aerosol with a pH of less than 4.5 usually will induce bronchospasm in a susceptible individual; aerosols with a pH between 4.5 and 5.5 will occasionally cause this problem. An aerosol with a pH between 5.5 and 7.0 is considered to be safe. Any aerosol having pH greater than 7.0 is to be avoided as the body's tissues are unable to buffer alkaline aerosols and as a result irritation with bronchospasm occurs.

The pH is equally important for stability of the formulation. Apparently at pH greater than 7.0 degradation of tobramycin occurs. In the stability studies of 0.225% saline 60 mg/ml tobramycin solution, described in Example 6, accelerated stability testing at 40° C. at pH 7.0 showed, at one month, obvious yellowing of the solution indicating the presence of chromophore degradation product. This finding was unexpected and not predicted by the literature on aminoglycoside degradation (*Drug Develop Industr. Pharm.*, 18:1423–36 (1992)). This reaction was less apparent at pH 5.5 or 6.5. At such pH, apparently, the degradation is not present or is much slower. For these reasons as well as for the avoidance of bronchospasm in patients, the optimum pH for the aerosol formulation was determined to be between pH 5.5 to pH 6.5.

The formulation of the invention is nebulized predominantly into particle sizes allowing a delivery of the drug into the terminal and respiratory bronchioles where the *Pseudomonas aeruginosa* bacterium resides (FIG. 1). For efficacious delivery of tobramycin to the lung endobronchial space of airways in an aerosol, the formation of aerosol particles having mass medium average diameter predominantly between 1 to 5 µ is necessary. The formulated and delivered amount of tobramycin for treatment and prophylaxis of endobronchial infections, particularly those caused by the bacterium *Pseudomonas aeruginosa*, must effectively target the sputum produced by the bacterium. The formulation must have a smallest possible aerosolizable volume able to deliver effective dose of aminoglycoside to the site of the infection. The formulation must additionally provide conditions which would not adversely affect the functionality of the airways. Consequently, the formulation must contain enough of the drug formulated under the conditions which allow its efficacious delivery while avoiding undesirable reaction. The new formulation according to the invention meets all these requirements.

The choice of the nebulizer is also critical. Among the available nebulizers, the jet nebulizers known as Sidestream®, obtained from Medicaid and Pari LC® obtained from Pari Respiratory Equipment, Richmond, Va., were found to produce an antibiotic aerosol with potentially respirable characteristics. Two ultrasonic nebulizers that produce appropriate particle size 1 to 5 µ, and have a 5 ml reservoir capacity, are the Aerosonic by DeVilbiss and UltraAire by Omron. These jet and two later ultrasonic nebulizer, can also be advantageously used in the invention.

The formulated dose of 60 mg/ml of one quarter diluted saline has been found to be optimal for the most efficacious delivery. Although in some instances both lower or higher doses, typically from 40–80 mg/ml may be advantageously used, the 60 mg/ml dose of tobramycin is preferred. A more concentrated tobramycin solution has three disadvantages. First, if the solution approaches the solubility of tobramycin, 160 mg/ml, precipitation on storage is expected. Second, a higher concentration of tobramycin than is clinically needed is economically disadvantageous. Thirdly, a more concentrated solution will increase the osmolarity of the solution, thus decreasing the output of the formulation with both jet and ultrasonic nebulizers. The alternative of a more concentrated solution in a smaller total volume is also disadvantageous. Most nebulizers have a dead space volume of 1 ml, i.e., that of the last 1 ml of solution is wasted because the nebulizer is not performing. Therefore, while for example, a 2 ml solution would have 50% wastage, the 5 ml solution (the capacity of the nebulizer) has only 20% wastage. Additionally, since there is no sufficient aerosolization of the drug into the small particles, the drug in large particles or as a solution is deposited in the upper airways and induces cough and may also cause bronchospasm. Large aerosol particles also limit the drug delivery.

The dose lower than 60 mg of tobramycin per ml of diluted saline is not sufficient to suppress the bacterium and to treat the infection. Lower concentrations of tobramycin will not be sufficiently effective in at least 90% of patients. This is due to variability of sputum tobramycin levels caused by anatomical variability among patients as observed in Examples 4 and 5, and also because the minimum inhibitory concentration of *Pseudomonas aeruginosa* also varies. As seen in Table 4, a dose of 300 mg total has been found to be optimal. Previously studied doses 80 mg, *Pedia Pulmonol.*, 6:91–8 (1989) were reported effective, however, the dose would be predicted to be efficacious in approximately sixty to seventy percent of patients initially. If any degree of drug resistance developed, only a small percentage of patients would be effectively treated.

The size of the aerosolozized particles was found to be critical. If the particles were larger than 1–5 µ than they impacted the upper airway in that they were deposited above the endobronchial space, in the oropharynx and in the mouth. As a result of this, the drug delivery was impaired, a large amount of the drug was wasted, the patient's treatment was slowed down or greatly impaired and the cost of the treatment was raised. Furthermore, drug deposited in the oropharynx is swallowed and there can be some absorption of aminoglycoside from the gastrointestinal tract. Since the ototoxicity and nephrotoxicity of aminoglycoside is cumulative, any absorption is disadvantageous to the patient.

According to the invention, aminoglycoside is formulated in a dosage form intended for inhalation therapy by patients with cystic fibrosis. Since the CF patients reside throughout the world, it is imperative that the formulation has reasonably long shelf-life. A storage conditions and packaging thus become important.

As discussed above, the pH of the solution is important in prevention of tobramycin degradation. The pH between 5.5 and 6.5, preferably at 6.0 was found to be most optimal from the storage and longer shelf-life point of view.

The formulation is typically stored in five-milliliter low-density polyethylene (LDPE) vials. The vials are aseptically filled using a blow-fill-seal process. The vials are sealed in foil overpouches, six per overpouch. This packaging scheme conveniently provides a three-day supply of product per overpouch, with a dose regimen of two treatments per day, one vial per treatment.

Stability of the formulation is another very important issue for efficacious formulation. If the drug is degraded before its aerosolization, smaller amount of the drug is delivered to the lung thus impairing the treatment as well as provoking conditions which could lead to development of resistance to aminoglycoside because the delivered dose would be too small. Moreover, tobramycin degradation products may provoke bronchospasm and cough. To prevent the degradation of tobramycin at the proposed concentration of 60 mg/ml and in order to provide acceptable stability, a product with low oxygen content is produced by packaging the LDPE vials in oxygen-protective packaging comprising foil overpouches, six vials per overpouch. Prior to vial filling, the solution in the mixing tank is nitrogen sparged and the annular overpouch headspace is nitrogen purged. In this way, both hydrolysis and oxidation of aminoglycoside is prevented.

II. Nebulizers

An indivisible part of this invention is a jet or ultrasonic nebulizer able to nebulize the formulation of the invention into aerosol particle size predominantly in the range from 1–5 µ. Predominantly in this application means that at least 70% but preferably more than 90% of all generated aerosol particles are within 1–5 µ range.

Two types of nebulizers such as jet and ultrasonic, can produce and deliver particles between the 1 and 5 µ particle size that is optimal for treatment of *Pseudomonas aeruginosa* infections are currently available. A jet nebulizer works by air pressure to break a liquid solution into aerosol droplets. An ultrasonic nebulizer works by a piezoelectric crystal that shears a liquid into small aerosol droplets. However, only some formulations of aminoglycosides and particularly tobramycin can be efficiently nebulized by both nebulizers as both devices are sensitive to the pH of the formulation and to its ionic strength. The formulations which can be nebulized typically must contain large amounts of the aminoglycoside which is delivered in large volumes of aerosol.

Prior art aerosolized formulations with higher concentrations of aminoglycoside (50 mg/ml or greater) have used normal saline solutions that are not as efficiently nebulized by an ultrasonic nebulizer.

While the range variety of nebulizers is available, only limited number of these nebulizers are suitable for the purposes of this invention. The suitable nebulizer for the purposes of this invention is illustrated in FIG. 3.

Figure 3:
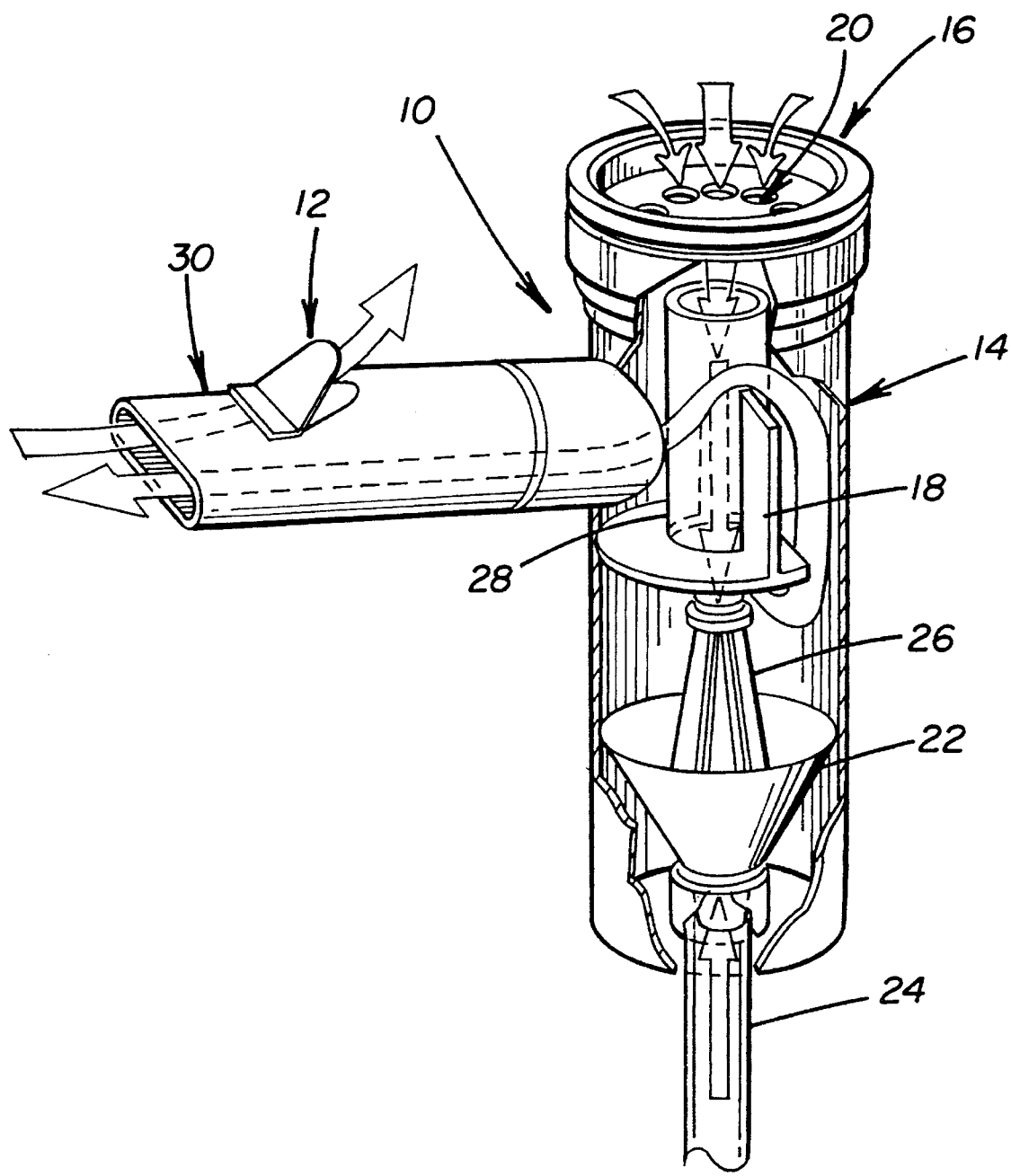
FIG. 3 depicts a jet nebulizer suitable for aerosolization of the concentrated aminoglycoside solution.

FIG. 3 shows the jet nebulizer 10 useful for aerosolization of tobramycin and other aminoglycosides to 18.

The liquid formulation is placed into the nebulizer cup 22 by removing and replacing the cup's cap (16). The cap 16 has one or more air intake holes (20) that allow entrainment of room air to Venturi chamber 28. Venturi chamber 28 allows entrained room air to mix with aerosol to increase drug delivery. Air supply tube 24, typically (8 l/M) is connected to nebulizer's liquid medicine cup 22. Air goes through the cup 22 into jet nebulizer orifice 26 where it creates aerosol by shearing the liquid solution into small threads of liquid that shatter into small particles when it hits a baffle 18. The nebulizer 10 further comprises a mouthpiece 30 for inhalation of aerosol. The mouthpiece contains flapper valve 12 to allow exhalation. The mouthpiece 30 is connected to the main body of the nebulizer 10.

To identify efficient and suitable nebulizer for use in the current invention, two separate studies were performed.

The first study, described below, was to determine in vitro which nebulizers meet criteria that are important for delivery of aerosolized antibiotics. Both ultrasonic and jet nebulizers were studied. The second study was to determine the pharmacodynamics of aminoglycoside in the sputum which is a measure of the efficacy of the aerosol delivery.

The major limitation of the Ultraneb 99 (DeVilbiss) ultrasonic nebulizer used for delivery of tobramycin formulation are its high-cost, waste of the drug and inconvenience. As seen from Table 1, this nebulizer requires 30 ml of the drug solution, and it has large, 1200 ml aerosol reservoir. In order for aminoglycoside aerosol therapy to be widely available and used by patients with cystic fibrosis in ambulatory or home setting, a more efficient and easier to use nebulizer is needed.

This study was the first step in testing whether the first jet nebulizer could be substituted for ultrasonic nebulizer and whether adequate sputum aminoglycoside levels can be obtained with a jet nebulizer. Subsequent studies included long-term clinical efficacy.

An in vitro comparative study evaluated a variety of commercially available jet nebulizers, including among others, the Acorn II® by Marquest, T-Updraft® by Hudson, Sidestream® by Medicaid, and Pari LC® by Pari. The PulmoAide® compressor was chosen because of its reliability and widespread use in the CF population.

A closer look at all these nebulizers revealed that most of them are relatively inefficient in delivering an inhalable mist. The three chosen nebulizers used in the clinical protocols, the ultrasonic DeVilbiss 99, the Pari LC jet and the Medicaid Sidestream jet, have shown properties suggesting that they could possibly deliver tobramycin aerosol into endobronchial space. Of the three, two jet nebulizers were clearly superior to the ultrasonic DeVilbiss. Therefore, they have been evaluated in vitro to determine which one of them could provide the greatest amount of drug to the airways and two jet nebulizers were found to meet the requirements.

A comparative characteristics of the Ultraneb 99 DeVilbiss (ultrasonic) and two of the jet nebulizers, the Sidestream and the Pari LC with the PulmoAide compressor, showing the best in vitro characteristics, are listed in Table 1.

TABLE 1

| | Comparative Characteristics of Different Nebulizers | | |
|---|---|---|---|
| Nebulizer | DeVilbiss 99 | Sidestream | Pari LC |
| Type | Ultrasonic | Jet | Jet |
| Airflow | 8 L/m | 8 L/m | 8 L/m |

TABLE 1-continued

| Comparative Characteristics of Different Nebulizers | | | |
|---|---|---|---|
| Nebulizer | DeVilbiss 99 | Sidestream | Pari LC |
| Liquid Reservoir | 30 ml | 5 ml | 5 ml |
| Time to Nebulize | 10–12 minutes | ~13 minutes(*) | 10 minutes(**) |
| Aminoglycoside Formulation | 20 mg/ml in ½ NS | 60 mg/ml in 1/4 NS | 60 mg/ml in 1/4 NS |
| Aerosol Reservoir | 1,200 ml | 30 ml | 30 ml |
| MMAD** | ~4–5 microns | ~2.2 microns | ~4–5 microns |
| Drug Dose/ml | 33 ± 1.8 mg | 30 ± 1.8 mg | 29 ± 5 mg |
| Total Drug Dose | 600 mg | 300 mg | 300 mg |

(*) Time to sputtering of jet
(**) Mass median aerodynamic diameter

As seen from Table 1, there are substantial differences between the ultrasonic and jet nebulizer systems. The two jet nebulizers require about six times smaller solution volume and do not have or require a large reservoir from which the aerosol can be inhaled. In terms of the dosage, for example, 600 mg dosage was used in the DeVilbiss 99 ultrasonic nebulizer while only one-half of that amount was found to be sufficient for use in jet nebulizer. To achieve the 600 mg dosage in jet nebulizer, the formulation required in a jet nebulizer would be 120 mg/ml in a 5 ml solution that is twice as large as is needed. Under these conditions, the solute tonicity would need to be decreased to maintain physiologic osmolarity of the solution. The osmolarity is the sum of the osmoles from the aminoglycoside and the saline in the solution. Physiologic osmolarity is a range that does not induce bronchospasm or cough.

Of the two jet nebulizers compared in Table 1, the Sidestream may be more efficient in delivery aminoglycoside to the lower airway because of the smaller (2.2 μ) particle size output. Conversely, the Pari LC produces a larger particle size (4.5 μ) at a higher output thus reducing the delivery time and patient's discomfort. Both jet nebulizers have a Venturi design which increases drug delivery within inspiration. The smaller equipment size decreases the fallout of aerosolized particles that occurs prior to inspiration by the patient. The jet nebulizers Sidestream and Pari LC also have the advantage of being available in both reusable disposable units.

As also seen in Table 1, all three nebulizers delivered about 30 mg/ml of aminoglycoside to the airways even though the ultrasonic DeVilbiss 99 nebulizer needed twice as much drug, that is 600 mg of aminoglycoside compared with 300 mg for the two jet nebulizers, for delivery of 33 mg/ml.

A high dose aminoglycoside regimen (600 mg) delivered via the ultrasonic DeVilbiss nebulizer demonstrated improved pulmonary function and thousand fold decrease in *P. aeruginosa* density in sputum following thirty days administration as described in NEJM, 328:1740 (1993). Although the administration of high dose aerosolized aminoglycoside via the ultrasonic DeVilbiss Ultraneb 99 nebulizer demonstrated safety and efficacy of the tobramycin aerosol treatment, patient and physician acceptance has been limited due to the cost of the drug required for this delivery system. In order to provide an adequate efficacious dose of aminoglycoside to the lower airway in a cost effective manner, that is utilizing lowest possible aminoglycoside doses, a nebulizer that delivers an aminoglycoside efficacy equivalence at least that of the ultrasonic Ultraneb 99 system is necessary.

The current invention tested and identified two jet nebulizers which are able to deliver the tobramycin efficacy equivalence by using only one-half of the dosage needed by ultrasonic nebulizer.

Based on in vitro testing of nebulizers under clinical conditions with a test lung set at tidal volume 0.6 L, respiratory rate 18 breaths/min, inspiratory to expiratory ratio 1:3 and a square wave breathing pattern, the predicted drug dose delivery to the patient was determined by measuring the amount of aminoglycoside collected following passage of the aerosolized drug through a filtration system that removes aerosolized particles >6.4 microns.

The above described studies also confirmed that the jet nebulizers are about 10% efficient under clinical conditions, while the ultrasonic nebulizer are only about 5% efficient. The amount deposited and absorbed in the lungs is a fraction of the 10% and therefore the danger of systemic exposure is low in spite of the large amounts of the drug in the nebulizer.

In addition to the above tested jet nebulizers, two small volume ultrasonic nebulizers, Aerosonic by DeVilbiss and UltraAire by Omron were also tested and found suitable for delivery of the formulation of the invention. These ultrasonic nebulizers differ from the UltraNebb 99 ultrasonic as they have a smaller reservoir and can use the smaller volume solution.

III. Efficacy

Delivery and efficacy of the aerosolized aminoglycoside formulation is determined and predicted by the presence and concentration of aminoglycoside in sputum. If the concentration of aminoglycoside found in sputum is sufficiently large to suppress the bacterial infection, then the formulation/nebulizer combination will be efficient in the delivery of the drug to the lung. However, if at the same time, the amount of drug which needs to be aerosolized is also very large to achieve therapeutic levels, then, quite obviously, the formulation is not that efficient and leads to the waste of the drug. The most efficient formulation is the one where the amount of aerosolized drug is sufficient in the vast majority of patients of more than 90%, where all or almost all of the drug is delivered into the site of infection, and where amount is still sufficient to suppress the bacteria in sputum. The measure of the efficacy in this instance is the finding sufficient amount of the nebulized drug in the sputum in the vast majority (>90%) of the patients in the population. Efficient tobramycin delivery is defined as achieving spectrum concentration ≧10 times the MIC of 90% *Pseudomonas aeruginosa* pathogens (i.e., 128 mg/ml) in ≧90% patients tested.

The second question of this study therefore concerned the appropriate target concentration of aminoglycoside in the sputum which is a measure of efficacy. Determination of target aminoglycoside concentrations needs to take into account the typical 10-fold variability of aminoglycoside concentration seen in sputum between patients due to intrinsic anatomic and physiologic factors. Such determination must also account for the range of median inhibitory concentration (MIC) observed in clinical isolates.

Studies examining the efficacy of aerosolized aminoglycoside consistently show improvement in CF patients. In the most extensive study to date described by inventor Smith in *N. Engl. J. Med.*, 328:1740 (1993), 71 patients took part in a multicenter, double-blind, placebo-controlled, three-period crossover trial to determine the efficacy of aerosolized aminoglycoside for the treatment of endobronchial infection due to *P. aeruginosa* in CF patients. The patients were divided into two groups. Group 1 received 600 mg of aerosolized aminoglycoside three times a day by ultrasonic nebulizer for 28 days. This was followed by a placebo for two consecutive, 28-day periods. Group 2 received a placebo for the first 28 days and was followed by aminoglycoside for two consecutive, 28-day periods.

A comparison of the data from Groups 1 and 2 following completion of the first 28-day period showed that aminoglycoside was associated with favorable changes in a variety of quantifiable tests including forced expiratory volume, forced vital capacity and a decrease in colony forming units (CFUs) of *P. aeruginosa* in sputum.

A comparison of the data following completion of the entire three-period study showed that significant improvement was associated with aerosolized tobramycin treatment. This improvement occurred to a greater extent after the first 28-day period. In all three periods, however, a reduction in the density of *P. aeruginosa* in the sputum by a factor of 100 was observed.

Previous studies have shown that sputum concentrations greater than 13,500 µg/gm can be achieved by inhalation.

IV. Pharmacokinetics and Clinical Studies

During the development of the current invention, having in mind a primary aim at achieving the greatest efficacy by using the smallest possible drug dosage, first the pharmacokinetics of tobramycin in sputum have been studied following aerosol administration to twenty patients with CF. Using the same inhalation protocol utilized in subsequent clinical trials i.e., a dose of 20 mg/ml tobramycin sulfate in 30 ml of half normal saline administered by ultrasonic Ultraneb 99 nebulizer for 200 inhalations, peak sputum levels were achieved 10–30 minutes after receiving the therapy. These levels ranged from 310.4 µg/gm to 5,941 µg/gm, with median level at 1,606 µg/gm). The sputum levels declined rapidly after 30 minutes, reaching a minimum at four hours.

Reviewing the MIC's for the isolates with the maximum density (right column) listed in Table 3, it is apparent that sputum levels obtained in the above study were unnecessarily high and the sputum levels lower than those achieved with the ultrasonic Ultraneb 99 nebulizer regimen would be sufficient. A sputum level of 128 µg/gm would be greater than or equal to the MIC for 98% of all isolates and approximately ten-fold greater than the MIC for 90% of all isolates. The aim of the efficiency protocol was, therefore, to compare several ultrasonic and jet nebulizer systems with the goal of achieving a sputum concentration of about 128 µg/gm but not lower or not much higher.

Following these preliminary studies, two clinical trials described in detail in Examples 3–5 were performed.

In the first clinical trial, as the first part of the study, pharmacodynamic assessments of aerosol delivery efficacy of two jet nebulizers were made with a primary aim to determine the appropriate target concentration of tobramycin in the sputum. This study concluded that the optimal tobramycin formulation is the one where the combination of a specific nebulizer with a specific formulation achieves a sputum tobramycin concentration about 128 µg/g in about 90% patients. Such concentration corresponds to 98% of minimum inhibitory concentration (MIC).

In the second part of the clinical study, two jet nebulizers, Sidestream and Pari LC were compared and evaluated with respect to their ability to achieve the sputum concentration of tobramycin between 128 µg/g and 1000 µg/g. Both jet nebulizers were found to be able to achieve a target concentrations of tobramycin in sputum when the formulation containing 300 mg in 5 ml in ¼ NS was used.

The clinical trial II confirmed the results obtained in the clinical trial I and compared the delivery of tobramycin formulation tested in clinical trial I, in two jet and 1 ultrasonic nebulizer. The dosages for jet nebulizers were 300 mg tobramycin/5 ml. The dosage for ultrasonic nebulizer was 600 mg/30 ml. Half dosage of tobramycin delivered by jet nebulizers was sufficient to achieve therapeutically effective concentration of tobramycin in the endobronchial space.

The clinical trials confirmed that by using the new tobramycin formulation in combination with jet nebulizers delivers sufficient concentration of tobramycin into endobronchial space to achieve suppression of endobronchial infection caused by *Pseudomonas aeruginosa*. The combination of the new formulation of tobramycin in ¼ normal saline is easily aerosolized by jet nebulizer and the produce aerosol particles have sizes predominantly between 1–5 µ. The combination of the new formulation with the jet nebulizer results in considerable improvement against prior art formulations and the delivery means. The combination provides higher efficacy, is more safe and provides savings up to 50% of drug necessary to achieve the same results than those achieved by prior art treatments.

UTILITY

The utility of this invention is that this small volume, high concentration formulation of aminoglycosides can be used by either a jet or hand-held ultrasonic nebulizer and deliver efficacious concentrations of the drug to the endobronchial space in people with chronic bronchitis and bronchiectasis due to aminoglycoside susceptible bacteria or other infections. The formulation is safe and very cost effective. Furthermore, the formulation is kept in a nitrogen environment and with pH controlled to provide adequate shelf life for commercial distribution.

EXAMPLE 1

Tobramycin Formulation

This example illustrates preparation of the formulation of the invention.

1. Hot water for injection was thoroughly flushed (WFI) through 20 L Millipore product vessel.

2. Tobramycin Potency (g/L) was assayed, $$mg/mg \times \frac{1,000 \text{ mg}}{1 \text{ mg}}$$

Tobramycin was added to product vessel.

3. The amount of tobramycin was weighed accurately into a wide mouth specimen bottle and label.

4. 11.25 kg of WFI was dispersed into a clean 20L Millipore product vessel.

5. With moderate agitation, 33.75 g sodium chloride, USP, was slowly added and mixed until dissolved.

6. WFI was added to the product vessel to 12 Kgs and mixed for 5 minutes.

7. With continual mixing, 100 mL 5N $H_2SO_4$ (sulfuric acid) was carefully added for each liter of WFI in the final formulation.

8. Product vessel was sparged with nitrogen ($N_2$).

9. After approximately 15 minutes of sparging, dissolved oxygen ($O_2$) was measured by continuous monitoring of dissolved oxygen in the tank, using a probe.

10. Measuring of dissolved $O_2$ was continued until five (5) consecutive measurements $\leq 3$ ppm dissolved $O_2$.

11. With continuous sparging of $N_2$ and moderate mixing, the tobramycin was added and mixed until dissolved.

12. 20 mL sample from product formulation was removed and pH was measured. Adjust product formulation to achieve a final pH value of 6.0.

13. An aliquot of product formula was sampled and analyzed for tobramycin concentration.

14. An aliquot of product formula and was analyzed for pH.

15. An aliquot of product formula was analyzed for dissolved $O_2$ (in triplicate).

16. When the batch met quality control testing criteria, the product was released.

EXAMPLE 2

Delivery of Tobramycin and Effect of Normal and Dilute Saline

This example illustrates the effect of normal and quarter strength diluted saline in the aerosolized amount of drug delivered over a ten-minute period.

To test output from a hand-held portable ultrasonic nebulizer, an UltraAirs by Omron was used. This ultrasonic nebulizer has a reusable medication cup that it is over the ultrasonic crystal. The medication cup was weighed, a 5 ml solution of tobramycin (60 mg/ml) was added and cup reweighed. The solute was either normal saline (0.9% w/v) or ¼ normal (0.225% w/v). After 10 minutes nebulization runs, the cup was reweighed. The output was the difference between pre- and post-weights. Each solute was tested 14 times. The attached table shows the results.

Statistical analysis of the results show that the ¼ normal solution delivers a higher amount of drug over a ten-minute period (p=0.031).

Results are shown in Table 2.

TABLE 2

Effect of Saline Dilution on Ultrasonic Nebulizer Delivery of Tobramycin
Comparison of 0.9% NS v. 0.22% NS

| | MEAN | ST. DEV | VAR | COEF/ VAR |
|---|---|---|---|---|
| Nondiluted 0.9% NS | 3.635714 | 0.583737 | 0.340749 | 0.160556 |
| 1/4 - diluted 0.22% NS | 4.070714 | 0.41174 | 0.1 6953 | 0.101147 |

Tobramycin formulated in diluted saline was delivered higher in higher amount than the one formulated in nondiluted saline.

EXAMPLE 3

Clinical Trial-I Pharmacodynamic Assessment of Aerosol Delivery Efficacy

This example illustrates clinical trial-pharmacodynamic assessment of aerosol delivery efficacy.

Study Design

This study was a one-year review of all microbiologic records at Children's Hospital in Seattle. All positive *Pseudomonas aeruginosa* culture data were collated that occurred in patients with Cystic Fibrosis. If multiple cultures from a single individual had been obtained, the first culture was taken as representative. A data base was then generated on the number of individuals and the respective characteristics of the level of tobramycin required to inhibit bacterial growth.

The primary aim of this clinical study concerned the appropriate target concentration of tobramycin in the sputum to treat the *Pseudomonas aeruginosa* infection. Target tobramycin concentrations need to take into account the typical 10-fold variability of tobramycin concentration seen in sputum between patients due to intrinsic anatomic and physiologic factors. They must also account for the range of median inhibitory concentration (MIC) observed in clinical isolates.

Tables 3 and 4 illustrate MIC obtained from the tobramycin resistant and common *Pseudomonas aeruginosa* isolates.

TABLE 3

Distribution of the MICs for the Most Tobramycin-resistant Isolate obtained from the Sputum of each Patient (n= 58)

| MIC | Isolate (*P. aeruginosa*) with Maximum MIC | |
|---|---|---|
| (μg/ml)* | # of Patients | Cumulative Frequency |
| .25 | 21 | 36% |
| .5 | 10 | 53% |
| 1 | 8 | 67% |
| 2 | 5 | 75% |
| 4 | 4 | 83% |
| 8 | 2 | 86% |
| 16 | 2 | 90% |
| 32 | 2 | 93% |
| 64 | 1 | 95% |
| 128 | 2 | 98% |
| 256 | 1 | 100% |

*MIC = Minimum Inhibitory Concentration

The MIC's of tobramycin for the isolates of *P. aeruginosa* from patients at Children's Hospital in Seattle ranged from 0.25 μg/ml to 256 μg/ml with an $MIC_{90}$ of 16 g/ml (Table 3). $MIC_{90}$ is the concentration of the drug which inhibits 90% of *Pseudomonas aeruginosa* isolates. Sputum samples from CF patients were cultured to produce individual colony forming units (CFUs). The MIC was then determined for individual CFUs. CFUs were considered different isolates if their MICs were different.

The frequency of these isolates (Table 4) shows that sputum levels lower than those achieved with the ultrasonic nebulizer (Ultraneb 99) regimen are sufficient to reach therapeutic levels. A sputum level of 128 μg/gm would be greater than or equal to the MIC for 98% of all isolates as seen in Table 3 and approximately ten-fold greater than the MIC for 90% of all isolates as seen in Table 4. An initial target concentration of tobramycin ten-fold greater than the MIC is necessary because sputum appears to bind up to 90% of tobramycins. The optimal tobramycin formulation is the one where a nebulizer and formulation combination that achieves a sputum concentration of tobramycin of >128 μg/gm in at least 56 of 60 CF patients.

TABLE 4

Distribution of the MICs for the most Common Isolate obtained from the Sputum of Each Patient (n = 58)

| MIC (μg/ml) | Isolate (*P. aeruginosa*) with Maximum Density | |
|---|---|---|
| | # of Patients | Cumulative Frequency |
| .25 | 26 | 45% |
| .5 | 10 | 63% |
| 1 | 9 | 78% |
| 2 | 3 | 83% |
| 4 | 2 | 86% |
| 8 | 2 | 90% |
| 16 | 2 | 93% |
| 32 | 1 | 95% |
| 64 | 1 | 97% |
| 128 | 2 | 98% |

TABLE 4-continued

Distribution of the MICs for the most Common Isolate obtained from the Sputum of Each Patient (n = 58)

| MIC (μg/ml) | Isolate (*P. aeruginosa*) with Maximum Density | |
|---|---|---|
| | # of Patients | Cumulative Frequency |
| 256 | 1 | 100% |

*MIC = Minimum Inhibitory Concentration

As seen in Tables 3 and 4, 128 μg/ml of tobramycin were found to achieve 98% of inhibition of the most resistant as well as the most common *Pseudomonas aeruginosa* isolates.

EXAMPLE 4

Study 2—Testing Nebulizers

A clinical study 2 of the clinical Trial I was conducted at the University of Washington to determine the tobramycin formulation required to achieve a sputum concentration between 128 μg/gm and 1000 μg/gm sputum at 10 min post-completion of aerosol administration from a Sidestream jet nebulizer using a PulmoAide compressor and a Pari LC jet nebulizer using a PulmoAide compressor.

Five CF patients received serial doses of 300 mg tobramycin (5 ml of a 60 mg/ml solution in ¼ NS) from each of the two jet nebulizers. The doses were separated by at least 2 days and not more than 5 days. Peak serum and sputum concentrations were assessed and results are seen in Tables 5 and 6.

TABLE 5

Sputum Concentrations Following Aerosol Administration of 300 mg Tobramycin in 5 ml of 1/4 NS

| Subject # | Jet Nebulizer | Sputum Tobramycin Concentrations (μg/gm) | | | |
|---|---|---|---|---|---|
| | | Baseline | 10 min.* | 1 hour* | 2 hours* |
| 001 | Sidestream | bql† | 792.8 | 1026.7 | 163 |
| | Pari LC | bql | 1595.9 | 481.8 | 416.8 |
| 002 | Sidestream | bql | 460.6 | 23.1 | 49.1 |
| | Pari LC | bql | 764.2 | 231.8 | 52.8 |
| 003 | Sidestream | bql | 162.5 | 180.5 | 58.1 |
| | Pari LC | bql | 133.7 | 110.7 | 92.5 |
| 004 | Sidestream | bql | 84.2 | 36.6 | 57.5 |
| | Pari LC | bql | 166.5 | 32.4 | 60.5 |
| 005 | Sidestream | bql | 1135.9 | 488.2 | 331.5 |
| | Pari LC | bql | 1395.6 | 186.8 | 131.8 |
| Mean/Std | bql | 527.2 ± 585.9 | | | |
| Dev | bql | 811.2 ± 677.2 | | | |

*Timed from completion of aerosol treatment.
† < 20 μg/gm

TABLE 6

Serum Concentrations Following Aerosol Administration of 300 mg Tobramycin in 5 ml of 1/4 NS

| Subject # | Jet Nebulizer | Serum Tobramycin μg/ml | | | ± % change $FEV_1$* |
|---|---|---|---|---|---|
| | | Baseline | 1 hour* | 2 hours* | 30 min* |
| 001 | Sidestream | not detected | 0.3 | 0.2 | −2.2% |
| | Pari LC | not detected | 0.2 | 0.3 | −1.2% |
| 002 | Sidestream | not detected | 0.2 | 0.2 | 0.0% |
| | Pari LC | not detected | 0.5 | 0.4 | 1.2% |
| 003 | Sidestream | not detected | 0.9 | 0.8 | −7.6% |

TABLE 6-continued

Serum Concentrations Following Aerosol Administration of
300 mg Tobramycin in 5 ml of 1/4 NS

| Subject # | Jet Nebulizer | Serum Tobramycin µg/ml | | | ± % change $FEV_1$* |
|---|---|---|---|---|---|
| | | Baseline | 1 hour* | 2 hours* | 30 min* |
| 004 | Pari LC | not detected | 0.6 | 0.5 | −0.6% |
| | Sidestream | not detected | 1.2 | 1.0 | −1% |
| | Pari LC | not detected | 0.5 | 0.4 | −2% |
| 005 | Sidestream | not detected | 1.6 | 1.0 | 0.0% |
| | Pari LC | not detected | 0.8 | 0.7 | −5% |

*Timed from completion of aerosol treatment.
< 20 µg/gm

The results show that an aerosolized tobramycin dose of 300 mg in 5 ml of 60 mg/ml in ¼ NS achieved the target concentration (>128 µg/gm sputum). This dosage was also considered extremely safe because serum concentrations (<1.6 µg/ml) were well below the recommended peak therapeutic serum concentrations, 5–10 µg/ml.

EXAMPLE 5

Clinical Trial II

This example shows results of clinical trial to confirm the results of clinical study I and II (Examples 3 and 4) and to compare efficacy, and pharmacokinetics of an tobramycin formulation administered by three different nebulizer delivery systems to patients with cystic fibrosis.

The primary aim of this study was to determine which of the three tested nebulizer systems, jet and ultrasonic, can aerosolize sufficient tobramycin sulfate to achieve a peak sputum tobramycin concentration of 128 µg/gm or greater measured 10 minutes after the completion of nebulization in at least 85% of patients with CF. The secondary aim was to determine whether the tobramycin concentration required to achieve a peak sputum concentration of 128 µg/gm or greater is safe and well tolerated by the patient.

Study Design

This was an open label, multicenter, randomized, crossover three arm study. Each arm was different nebulizer delivery system. Two arms deliver the same tobramycin formulation.

1. Standard Method: Ultrasonic DeVilbiss nebulizer containing a 30 ml solution of 20 mg/ml tobramycin in ½ normal saline (NS) inhaled for 200 inspirations. Ultrasonic DeVilbiss nebulizer containing a 30 ml solution of 20 mg/ml tobramycin in ½ NS inhaled for 200 inspirations. The ultrasonic formulation contains ½ NS rather than ¼ NS because the lower tobramycin concentration maintains a similar osmolality in both solutions 2. Test Method A: Sidestream jet nebulizer with PulmoAide compressor (at 8 L/minute) containing a 5 ml solution of 60 mg/ml tobramycin of ¼ NS inhaled until sputtering of nebulizer. The number of inhalations required as recorded.

3. Test Method B: Pari LC Jet nebulizer with PulmoAide compressor (at 8 L/minute) containing a 5 ml solution of 60 mg/ml tobramycin in ¼ NS until sputtering of nebulizer. The number of inhalations required was recorded.

Selection of Patients

A total of 60 patients were enrolled. Four medical centers participated in patient enrollment. All patients received each of the three aerosolized tobramycin regimens in random order. Each site was able to enroll a minimum of size patients. Patients, makes and/or females, with underlying disease of cystic fibrosis were eligible to participate in this study.

Formulation

The tobramycin sulfate preservative free (Lilly®), adjusted to pH 6.95±0.05, was supplied by Home Health Care of Washington (HHCW) in a plastic container sealed inside a foil bag.

Aerosol Nebulizer Devices

Nebulizer was either sidestream jet nebulizer with PulmoAide compressor (at 8 L/minute), Pari LC nebulizer with PulmoAide compressor (at 8 L/minute).

Test Drug Dosage

1. Standard Method: Ultrasonic DeVilbiss "Ultraneb 99" nebulizer containing 30 ml solution of 20 mg/ml tobramycin in ½ NS (the ultrasonic formulation contains ½ NS rather than ¼ NS because of the lower tobramycin concentration, thus maintaining a similar osmolality in both solutions) inhaled for 200 inspirations. The nebulizer was allowed to run for one minute prior to inhalations to allow output to be linear.

2. Test Method A: Sidestream jet nebulizer with PulmoAide compressor (at 8 L/minute) containing a 5 ml solution of 60 mg/ml tobramycin in ¼ NS inhaled until sputtering of nebulizer.

3. Test Method B: Pari LC nebulizer with PulmoAide compressor (at 8 L/minute) containing a 5 ml solution of 60 mg/ml tobramycin in ¼ NS until sputtering of nebulizer.

Efficacy and Safety Assessment

In this study, the following efficacy and safety parameters were assessed were:

The efficacy was determined for each nebulizer by measuring concentration of tobramycin in sputum 10 minutes after completion of nebulization. Concentration of ≧128 µg/gm of sputum was considered adequate.

The safety parameters assessed:

1. Incidence of treatment related adverse reactions occurring during the administration of the aerosolized tobramycin by the different nebulizer delivery systems.

2. Acute bronchospasm at the time of drug administration.

3. Absorption of tobramycin into the systemic circulation.

4. Pari LC Jet nebulizer with PulmoAide compressor (at 8 L/min) containing a 5 ml solution of 60 mg/ml tobramycin sulfate in ¼ NS Test Method B.

Sixty patients were enrolled. Each patient received, in random order, one administration from each nebulizer delivery system. Each aerosol administration was separated by a minimum of 48 hr. Sputum samples were collected at baseline, 10 minutes, 1 hr and 2 hr post-completion of the aerosol drug administration to measure tobramycin concentration. Serum samples were collected at baseline, 1 hr and 2 hr post-completion of aerosol administration to measure tobramycin levels. Airway irritation and acute bronchospasm were assessed by measuring spirometry immediately prior to and 30 min post-completion of aerosol administration. A decrease in FEV1>15% in the 30 min spirometry test was considered evidence of bronchospasm.

The primary objective of this study was to determine if the jet nebulizers tested can aerosolize sufficient tobramycin sulfate to achieve a peak sputum tobramycin concentration of 128 µg/gm or greater in at least 85% of patients with CF measured 10 minutes after the completion of nebulization. The dose used with the ultrasonic nebulizer (20 mg/ml in 30 ml ½ NS) as used in previous studies was is included as a control. The dose, both the concentration and volume, for the jet nebulizers was based upon the study described in Example 4.

The second objective was to determine whether the tobramycin concentration required to achieve a peak sputum concentration of 128 µg/gm or greater is safe and well tolerated by the patient. Safety was defined as a lack of acute bronchospasm and minimal systemic absorption.

The ultrasonic formulation (Standard Method) contained ½ NS rather than ¼ NS because of the lower high dilution and thus tobramycin concentration, thus maintaining a similar osmolality in both solutions.

Patient Treatment

All patients with underlying disease of cystic fibrosis (CF), confirmed at entry by the inclusion/exclusion criteria specified in this protocol, were eligible for enrollment into the study. Investigators at the participating CF centers selected patients that meet all of the inclusion criteria and one of the exclusion criteria.

Eligible patients were admitted to the study center on the day of the study and receive aerosol therapy if they fulfilled entrance criteria.

Physical exam was administered by a physician or RC nurcerior to initial aerosol treatment only.

Vital signs, height, weight, oximetry, assessment of current respiratory status and brief medical history were used.

Sputum and serum samples were collected to measure baseline tobramycin concentrations.

Patients sat upright and used nose clips during the aerosol administration. The total duration of time and the number of inhalations required to complete the aerosol treatment were recorded. Any evidence of wheezing or respiratory distress were recorded as well as number of rest periods required by the subject because of dyspnea or excessive coughing during the administration period.

Immediately after completing the aerosol therapy, the subject rinsed with 30 ml of normal saline through the mount, gargled for 5-10 seconds and expectorated the rinse. This was repeated for a total of three rinses. Sputum specimens were collected at 10 minutes after rinsing oral cavity and 2 hours after completion of the aerosol drug administration. Serum was collected at 1 and 2 hours after completion of the aerosol drug administration for determination of the tobramycin levels. Spirometry was obtained 30 minutes following completion of the aerosol drug administration. Following the last aerosol treatment of the study, patients received a brief physical exam after post-spirometry has been measured.

TABLE 7

| | Grand Means for 20 Patients | | | |
|---|---|---|---|---|
| Treatment | Time | Mean | Std Dev | % RSD |
| Sidestream | 0 hr | 0 | 0 | nq |
| | 10 min | 465.3 | 463.8 | 100 |
| | 1 hr | 75.7 | 118.6 | 157 |
| | 2 hr | 88.8 | 123.8 | 139 |
| Pari LC | 0 | 0 | 0 | nq |
| | 10 min | 639.1 | 521.3 | 82 |
| | 1 hr | 117.0 | 173.3 | 148 |
| | 2 hr | 77.6 | 89.3 | 115 |
| Ultra Neb | 0 hr | 0 | 0 | nq |
| | 10 min | 1335.7 | 1042.8 | 78 |
| | 1 hr | 360.0 | 352.4 | 98 |
| | 2 hr | 158.8 | 163.3 | 103 |

% RSD
µg

These are the grand means of means from four different centers of sputum of tobramycin levels from 20 patients after nebulization. Of note, Sidestream and Pari LC data are using the novel 300 mg (60 mg/ml) in 5 ml 0.225 NS formulation, the UltraNeb, a high (30 ml) volume of 600 mg in 0.45% NS.

The results of this study indicate that this formulation, when used with a jet nebulizer, delivers concentrations of tobramycin to the endobronchial space that are in the efficacious range based on the known relationship between MIC's, sputum tobramycin levels and clinical efficacy.

EXAMPLE 6

Stability of Tobramycin Formulation

An accelerated stability study of tobramycin 60 mg/ml in 0.225% NS in LDPE vials, packaged in a nitrogen enriched environment, was carried out for 35 days at 40° C. The higher temperature was chosen to accelerate any degradation process. Vials at target pH 515, 6.5 and 7.0 were studied at Day 0 and Day 35. Color was examined by KS scale. Results are in Table 8.

TABLE 8

| Results of 35 Day Stability Study at 40° C. | | | | |
|---|---|---|---|---|
| Target pH | N | Time (days) | Actual pH (Mean) | Color KS units (Mean) |
| 5.5 | 3 | 0 | 5.55 | 13 |
| 5.5 | 5 | 35 | 5.51 | 104 |
| 6.5 | 3 | 0 | 6.57 | 12 |
| 6.5 | 5 | 35 | 6.56 | 107 |
| 7.0 | 3 | 0 | 7.07 | 13 |
| 7.0 | 5 | 35 | 7.04 | 171* |

*p < .05 compared to 5.5 and 6.5. KS units:

LDPE vials of three pH levels or 60 mg/ml tobramycin in 0.225% NS, 5 ml total volume storage in foil overpouch nitrogen enriched environment. Color and actual pH testing was done at time) and after storage for 35 days at 40° C.

These results are surprising as there is a pH dependence on color formulation and there is color formulation. Previous work by Brandl M and Gu L, Drug Develop Industr. Pharm., 18:1423-36 (1992), details that the major degradation process for tobramycin is oxygen dependent. Therefore, we chose to package in a nitrogen enriched environment. The observation that color, an early marker of degradation and an undesirable product characteristic, occurs is surprising. The pH dependence of this reaction teaches that the optimal pH for the tobramycin formulation is in the pH 5.5 to 6.5 range.

Furthermore, the rapid coloring of the solution at 40° C. teaches that storage at lower temperatures, including refrigeration, is desirable.

What is claimed is:

1. An aerosol formulation for suppression and inhibition of at least 95% of susceptible bacteria in endobronchial space of a patient suffering from the endobronchial infection, said formulation comprising from about 200 mg to about 400 of aminoglycoside dissolved in about 5 ml of solution containing about 0.225% of sodium chloride;

said formulation having pH between about 5.5 and 6.5;

said formulation administered by aerosolization using a jet or ultrasonic nebulizer able to produce predominantly aerosol particle size between 1 and 5 µ.

2. The aerosol of claim 1 wherein the pH is 6.0.

3. The aerosol of claim 2 wherein the nebulizer is jet nebulizer.

4. The aerosol of claim 2 wherein the nebulizer is ultrasonic nebulizer.

5. An aerosol formulation for suppression and inhibition of at least 95% of *Pseudomonas aeruginosa* bacteria in endobronchial space of a patient suffering from the *Pseudomonas aeruginosa* infection, said formulation comprising about 300 mg of tobramycin dissolved in about 5 ml of solution containing 0.225% of sodium chloride;

said formulation having Ph between about 5.5 and 6.5;

said formulation administered by aerosolization using a jet or ultrasonic nebulizer able to produce predominantly aerosol particle size between 1 and 5 µ.

6. The aerosol of claim 5 wherein the Ph is 6.0.

7. The aerosol of claim 6 wherein the nebulizer is jet nebulizer.

8. The aerosol of claim 6 wherein the nebulizer is ultrasonic nebulizer.

9. A method for treatment of *Pseudomonas aeruginosa* bacteria end bronchial infections by providing patient in need of such treatment an aerosol formulation comprising about 300 mg of tobramycin dissolved in about 5 ml of solution containing 0.225% of sodium chloride;

said formulation having pH between about 5.5 and 6.5;

said formulation administered by aerosolization using a jet or ultrasonic nebulizer able to produce predominantly aerosol particle size between 1 and 5 µ.

10. The method of claim 9 wherein the pH of the aerosol formulation is about 6.0.

11. The method of claim 10 wherein the nebulizer used for administration of the aerosol formulation is the jet nebulizer.

12. The method of claim 10 wherein the nebulizer used for administration of the aerosol formulation is the ultrasonic nebulizer.

13. A method for treatment of *Pseudomonas aeruginosa* bacteria endobronchial infections by providing patient in need of such treatment an aerosol formulation comprising about 200 to about 400 mg of aminoglycoside dissolved in about 5 ml of solution containing 0.225% of sodium chloride;

said formulation having pH between about 5.5 and 6.5;

said formulation administered by aerosolization using a jet or ultrasonic nebulizer able to produce predominantly aerosol particle size between 1 and 5 µ.

14. The method of claim 13 wherein the pH of the aerosol formulation is about 6.0.

15. The method of claim 14 wherein the nebulizer used for administration of the aerosol formulation is the jet nebulizer.

16. The method of claim 14 wherein the nebulizer used for administration of the aerosol formulation is the ultrasonic nebulizer.

* * * * *

UNITED STATES PATENT AND TRADEMARK OFFICE
CERTIFICATE OF CORRECTION

PATENT NO. : 5,508,269
DATED : April 16, 1996
INVENTOR(S) : Arnold L. Smith, et. al.

It is certified that error appears in the above-indentified patent and that said Letters Patent is hereby corrected as shown below:

Abstract, line 7, delete "by a produced";

Column 1, line 61, correct "Infections" to --Infectious--;

Column 2, line 5, correct "doses" to --dose-- and "administration" to --administrations--;

line 38, delete "of";

line 39, change "sizes" to --size--;

Column 3, line 5, delete "The" and change "plugging" to --Plugging--;

line 36, delete "visit";

line 37, insert --visits-- after "hospital";

Column 6, line 5, change "an" to --any--;

line 35, insert --of-- between "drug" and "choice";

line 38, insert --hundred-- after "four";

line 54, change "is" to --in--;

line 63, change "wells" to --well--;

Column 8, line 1, delete "two later";

UNITED STATES PATENT AND TRADEMARK OFFICE
CERTIFICATE OF CORRECTION

PATENT NO. : 5,508,269
DATED : April 16, 1996
INVENTOR(S) : Arnold L. Smith, et al.

It is certified that error appears in the above-indentified patent and that said Letters Patent is hereby corrected as shown below:

line 2, change "nebulizer" to --nebulizers--;

line 43, change "than" (second occurrence) to --then--;

line 59, delete "A" and change "storage" to --Storage--;

Column 9, line 54, before "18" insert --aerosol having particle size predominantly in 1-5$\mu$ region. Nebulizer 10 consists of the outside case 14, mouthpiece 30, nebulizer cup 22 covered with cap 16, venturi chamber 28, air supply tube 24, liquid medicine cup 22 and baffle--;

Column 11, lines 23 and 24, delete "in a jet nebulizer";

line 32, insert --of-- after "delivery";

Column 14, line 27, delete "by";

Column 16, line 2, delete the first "higher";

Column 21, line 20, delete "is";

line 39, change "meet" to --met--;

Column 22, line 43, change "515" to --5.15--;

Column 23, line 36, change "Ph" to --pH--;

line 40, change "Ph" to --pH--;

UNITED STATES PATENT AND TRADEMARK OFFICE
CERTIFICATE OF CORRECTION

PATENT NO. : 5,508,269
DATED : April 16, 1996
INVENTOR(S) : Arnold L. Smith, et al.

It is certified that error appears in the above-indentified patent and that said Letters Patent is hereby corrected as shown below:

Column 24, line 6, change "end bronchial" to --endobronchial--

Signed and Sealed this

Third Day of September, 1996

Attest:

BRUCE LEHMAN

Attesting Officer

Commissioner of Patents and Trademarks